(12) United States Patent
Rogers

(10) Patent No.: US 8,496,648 B2
(45) Date of Patent: Jul. 30, 2013

(54) STIFFENING ASSEMBLY

(75) Inventor: Theodore W. Rogers, Alameda, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 1464 days.

(21) Appl. No.: 12/127,143

(22) Filed: May 27, 2008

(65) Prior Publication Data

US 2009/0299343 A1    Dec. 3, 2009

(51) Int. Cl.
*A61B 17/00* (2006.01)
*A61B 19/00* (2006.01)

(52) U.S. Cl.
CPC ................................ *A61B 19/22* (2013.01)
USPC .......................................................... 606/1

(58) Field of Classification Search
None
See application file for complete search history.

(56) References Cited

U.S. PATENT DOCUMENTS

| | | | |
|---|---|---|---|
| 4,815,450 A | 3/1989 | Patel | |
| 5,337,733 A | 8/1994 | Bauerfeind et al. | |
| 5,759,151 A | 6/1998 | Sturges | |
| 7,060,199 B2 | 6/2006 | Woydt et al. | |
| 7,598,652 B2 | 10/2009 | Kornbluh et al. | |
| 2002/0120178 A1* | 8/2002 | Tartaglia et al. | 600/114 |
| 2004/0054322 A1 | 3/2004 | Vargas | |
| 2006/0192465 A1* | 8/2006 | Kornbluh et al. | 310/800 |
| 2008/0065105 A1 | 3/2008 | Larkin et al. | |
| 2008/0091170 A1 | 4/2008 | Vargas et al. | |
| 2009/0030282 A1 | 1/2009 | Garcia et al. | |

OTHER PUBLICATIONS

U.S. Appl. No. 60/552,456, filed Mar. 12, 2004, Kornbluh, Roy D. et al.
U.S. Appl. No. 60/952,162, filed Jul. 26, 2007, Garcia, Pablo et al.
Vertut, Jean et al., Robot Technology: Teleoperation and Robotics Evolution and Development, 1986, vol. 3A, 332 pages, English translation Prentice-Hall, Inc., Inglewood Cliffs, NJ, USA.

* cited by examiner

*Primary Examiner* — Bethany Barham

(57) ABSTRACT

A stiffenable structure is made of longitudinal beams that are positioned around a longitudinal axis. In one state, the longitudinal beams are bendable so that the structure is bendable. As the structure bends, the longitudinal beams slide longitudinally with reference to one another. In a second state, the beams are clamped in a fixed position relative to one another so that the structure is stiffened. In some aspects the longitudinal beams are made of two or more longitudinal laminar elements. As each beam bends, the laminar elements slide longitudinally with reference to one another. Each beam, and accordingly the structure, is stiffened by preventing the laminar elements from sliding longitudinally relative to one another.

26 Claims, 7 Drawing Sheets

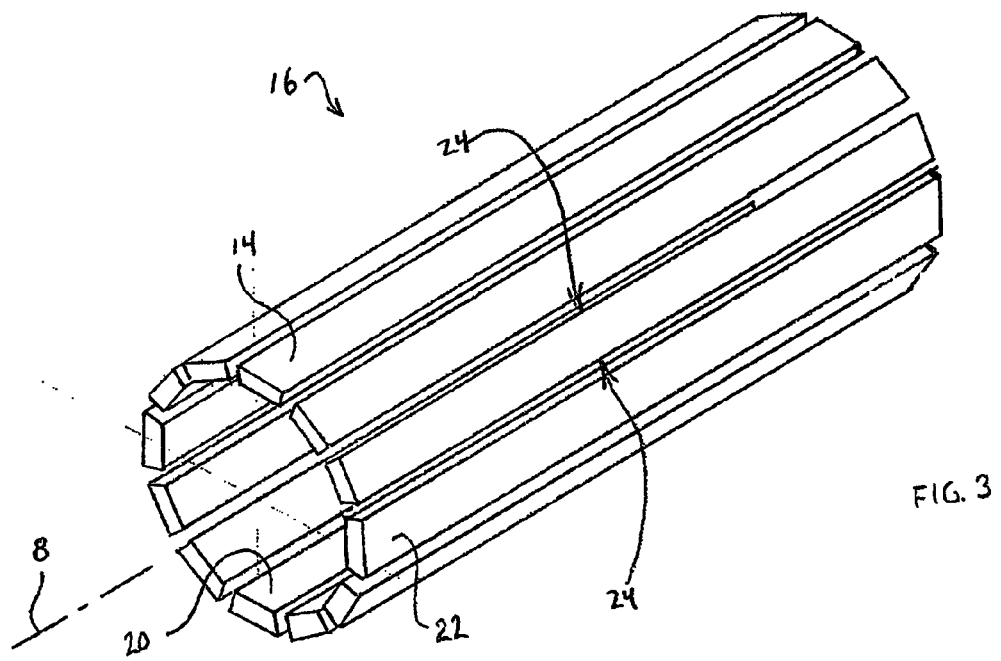
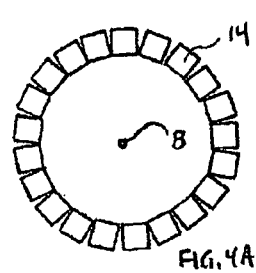
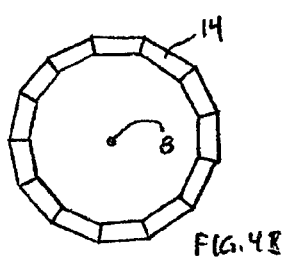
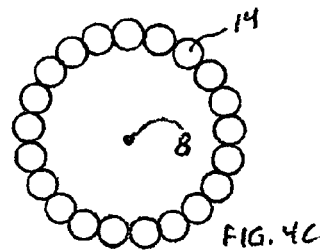
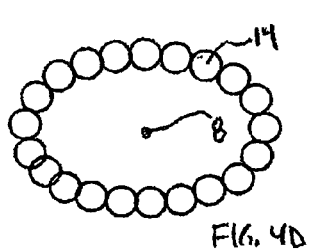
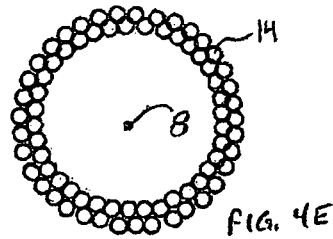
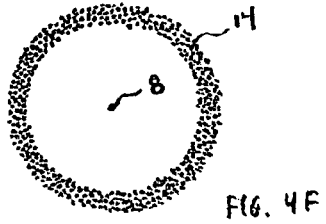
FIG. 3
FIG. 4A  FIG. 4B  FIG. 4C
FIG. 4D  FIG. 4E  FIG. 4F

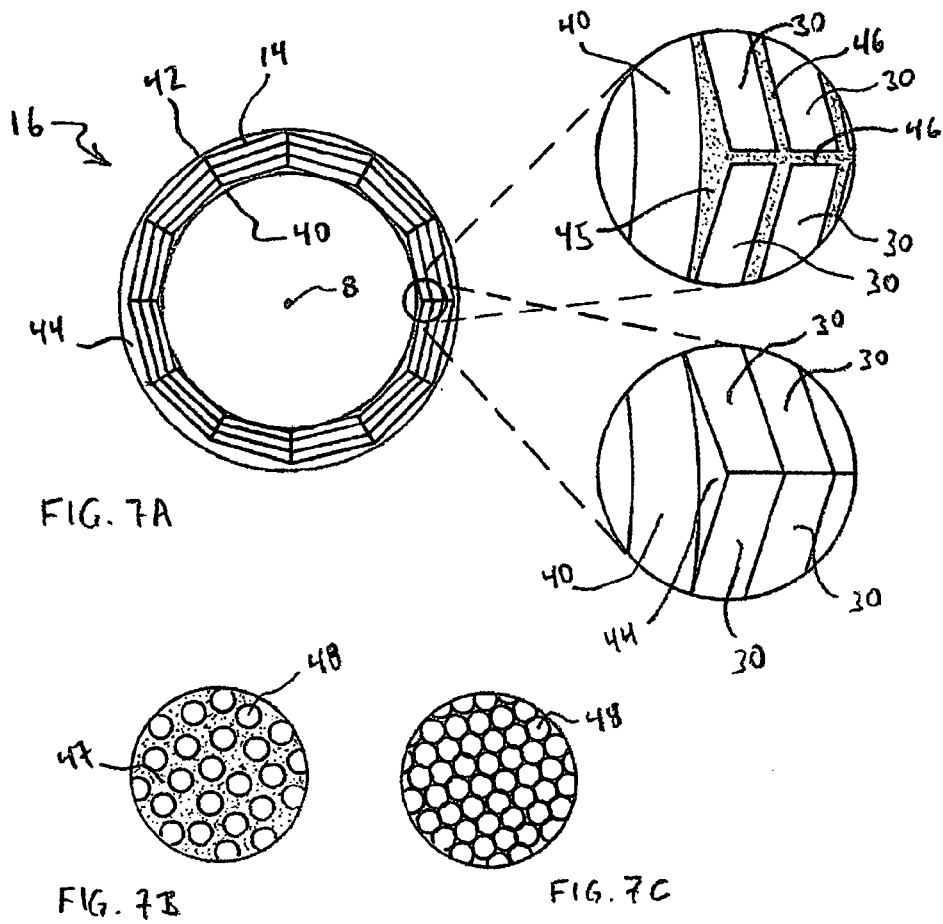
FIG. 7A
FIG. 7B
FIG. 7C
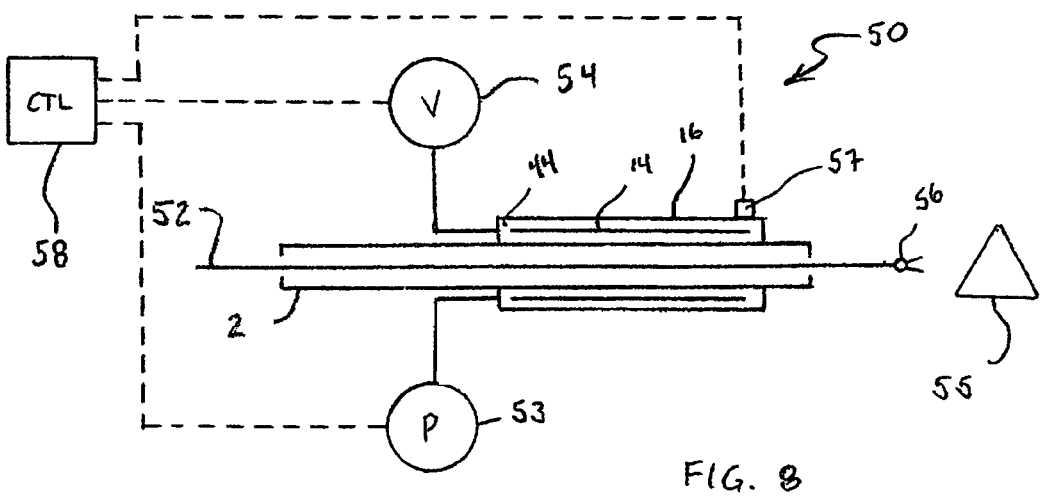
FIG. 8

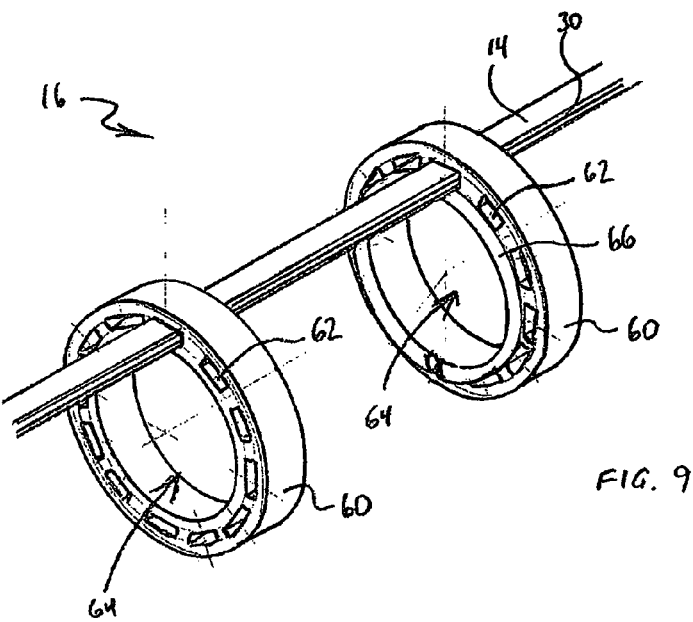
FIG. 9
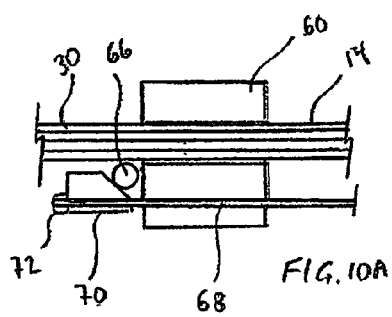
FIG. 10A
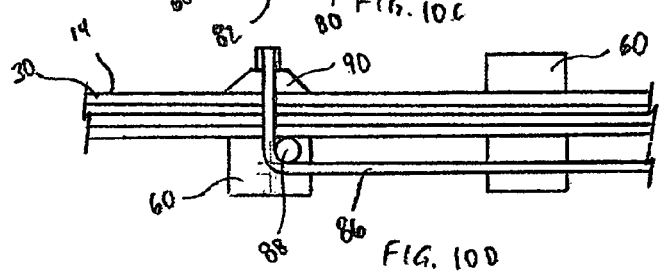
FIG. 10B
FIG. 10C
FIG. 10D

STIFFENING ASSEMBLY

BACKGROUND

1. Field of Invention

This invention relates to devices that may be varied between bendable and stiffened states, and more particularly to such stiffenable assemblies in tubular arrangements in devices for minimally invasive surgery.

2. Art

Minimally invasive surgical tools, such as those used for laparoscopic surgery, are often substantially rigid. Consequently, their reach is limited. To achieve useful triangulation of instruments at an internal surgical site, instruments must be inserted through multiple ports in the patient's body wall.

Flexible endoscopes that allow passage of two or more instruments to an internal surgical site are being used for surgery because such use requires only a single entry port into the body. But endoscopes typically lack rigidity and lack instrument triangulation at the distal end of the endoscope. Since the surgical instruments experience reactive forces from tissue (e.g., when retracting, suturing, etc.), some endoscopes rely on bracing against surrounding tissue to provide a stable base for the instruments. Other endoscopes rely on a stiffening/rigidizing mechanism. For instance, cables used to steer the endoscope may be locked in position or tensioned to increase friction in the endoscope's joints in order to stiffen the endoscope. But surrounding tissue used for bracing may be soft, and small control cables are subject to stretching due to the moment loads at the endoscope's distal end. Accordingly the flexible endoscope may only be made a limited amount more stiff than its flexible state. In addition, longitudinal tension on control cables used to increase friction between an endoscope's joints may cause the distal tip of the endoscope to move.

What is desired, therefore, is a structure that is significantly stiffer in a rigid state than in a flexible state. It is further desired that the structure be rigidizable in various shapes—bent or straight—and that such rigidizing does not affect the shape.

SUMMARY

A stiffenable structure is made of longitudinal beams that are positioned around a longitudinal axis to form a tube. The longitudinal beams are bendable, and in one state the beams are able to slide longitudinally relative to one another so that the structure is bendable. In a second state, the longitudinal beams are clamped in a fixed position relative to one another so that the structure is stiffened in a desired two- or three-dimensional curved shape. In some aspects the stiffenable structure is positioned around a guide that directs one or more minimally invasive surgical instruments to a surgical site. The guide may be an endoscope or other flexible structure, which may be steerable.

The longitudinal beams may be clamped in a fixed position in various ways, including the use of vacuum, so that ambient pressure compresses the beams, and the use of various mechanical clamping implementations, such as by cable tension or by the use of an expandable material. The beams may be clamped in a fixed position relative to one another by clamping them against one another or by clamping them to an intermediate structure, such as a bulkhead.

In some aspects the longitudinal beams are made of two or more longitudinal laminar elements. As each beam bends, the laminar elements slide longitudinally with reference to one another. Each beam is stiffened by clamping the laminar elements against one another.

Aspects of the invention may be used for minimally invasive surgical devices, such as surgical instrument guide tubes. Stiffening the distal end of a guide tube creates a stable platform to counteract reactive forces on surgical instruments during surgery, thus allowing a surgeon to effectively perform surgical tasks such as suturing and repeatedly grasping, pulling, and releasing tissue.

BRIEF DESCRIPTION OF THE DRAWINGS

FIG. 3 is an exploded perspective diagrammatic view of bendable longitudinal beams in a stiffening mechanism.

FIGS. 4A-4F are diagrammatic cross-sectional end views that illustrate various cross sectional shapes of longitudinal beams and arrangements of the beams around a longitudinal axis.

FIG. 7A is a diagrammatic cross-sectional view, with details that illustrate two clamping states, that shows longitudinal beams arranged in a stiffening assembly around a longitudinal axis, and the longitudinal beams are positioned between an inner wall and an outer wall. FIGS. 7B and 7C are details of another implementation of the clamping state details shown in the FIG. 7A illustration.

FIG. 8 is a schematic view of a vacuum clamping system for a minimally invasive surgical assembly.

FIG. 9 is a diagrammatic perspective view of another aspect of a stiffenable assembly in which intermediate structures (e.g., bulkheads) are used.

FIGS. 10A-10D are diagrammatic cross-sectional views that illustrate various aspects and implementations of clamping mechanisms.

DETAILED DESCRIPTION

This description and the accompanying drawings that illustrate aspects and embodiments of the present invention should not be taken as limiting—the claims define the protected invention. Various mechanical, compositional, structural electrical, and operational changes may be made without departing from the spirit and scope of this description and the claims. In some instances, well-known circuits, structures, and techniques have not been shown or described in detail in order not to obscure the invention. Like numbers in two or more figures represent the same or similar elements.

Further, this description's terminology is not intended to limit the invention. For example, spatially relative terms—such as "beneath", "below", 'lower', "above", "upper", "proximal", "distal", and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

A. Stiffening

Figure 1:
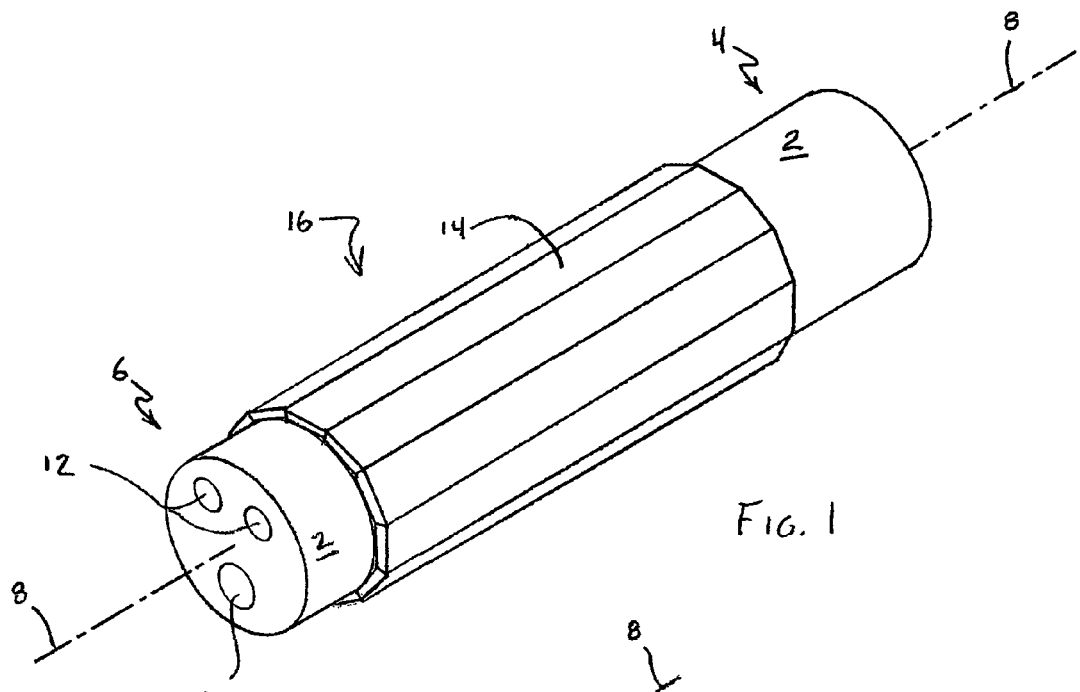
FIG. 1 is a diagrammatic perspective view that illustrates a general configuration of an aspect of the invention.

FIG. 1 is a diagrammatic perspective view that illustrates a general configuration of an aspect of the invention. FIG. 1 shows a flexible guide 2 having a proximal end 4 and a distal end 6. A longitudinal axis 8 is defined between the proximal and distal ends. Guide 2 is depicted as having at least one longitudinal channel 10 that extends from the proximal end (or nearly so) to the distal end (or nearly so). The single channel 10 shown in FIG. 1 is illustrative of one or more channels, which may be of various and differing diameters. Such channels may be used for, e.g., introducing surgical tools and equipment (e.g., surgical instruments, needle and suture, and the like) to a surgical site, introducing fluid (gas, liquid) to the surgical site, or removing matter from the surgical site (e.g., using suction, biopsy sampling, and the like).

In one aspect, guide tube 2 is an endoscope. Accordingly, guide 2 is depicted in FIG. 1 as including an illustrative distal end stereoscopic vision system 12. Vision system 12 is illustrative of various endoscopic vision systems that may be used, including direct viewing optical systems and electronic imaging systems with image capture components at either the proximal and distal ends. Vision systems may be mono- or stereoscopic. Steerable, flexible endoscopes are known and may be supplied by, e.g., Olympus Corporation (JP), Karl Storz GmbH & Co. KG (DE), or other vendors.

Guide 2 need not be an endoscope, however, and may be any flexible device that helps guide another device (e.g., a minimally invasive surgical instrument having an outer diameter of approximately, e.g., 2 mm, 5 mm, 8 mm, and similar sizes) from the proximal end to the distal end. Further, some or all of guide 2 may be steerable. For example, in some cases only the distal end is actively steerable, although the entire length of guide 2 may be flexible. In other cases the entire length of guide 2 may be steerable. In all cases, the lengths of the steerable sections in the guide may differ from one another. Illustrative steering mechanisms include manually or servomotor operated cables coupled to various links that form guide 2, as is known in the art (see e.g., U.S. Pat. No. 3,060,972 (filed 22 Aug. 1957), which illustrates basic cable steering principles, and which is incorporated herein by reference. Other steering mechanisms may include the use of shape memory alloy (e.g., Nitinol), electroactive polymers ("artificial muscle"), components positioned by externally generated magnetic forces, and the like. Examples of known steerable guides in the medical device field are steerable endoscopes and catheters. Steerable, flexible structures are further illustrated by U.S. Pat. No. 5,251,611 (filed 7 May 1991), which is incorporated by reference.

The term "flexible" includes devices that have many short pivotally coupled links that function as "vertebrae", which is how many commercial endoscopes are constructed, and also devices that are continuously curving, such as a bendable rubber tube.

In some instances guide 2 itself may be transitioned between a relatively lesser stiffness (flexible) to a relatively higher stiffness (effectively rigid). Such a transition between flexible and rigid states may be done by, e.g., increasing friction between jointed elements by applying tension to cables, or by holding an activation mechanism (e.g., hand wheel, servomotor) in place. Servomotors may be mechanically stabilized, e.g., by "braking" or "clutching", or they may be stabilized using software control.

Figure 2A:
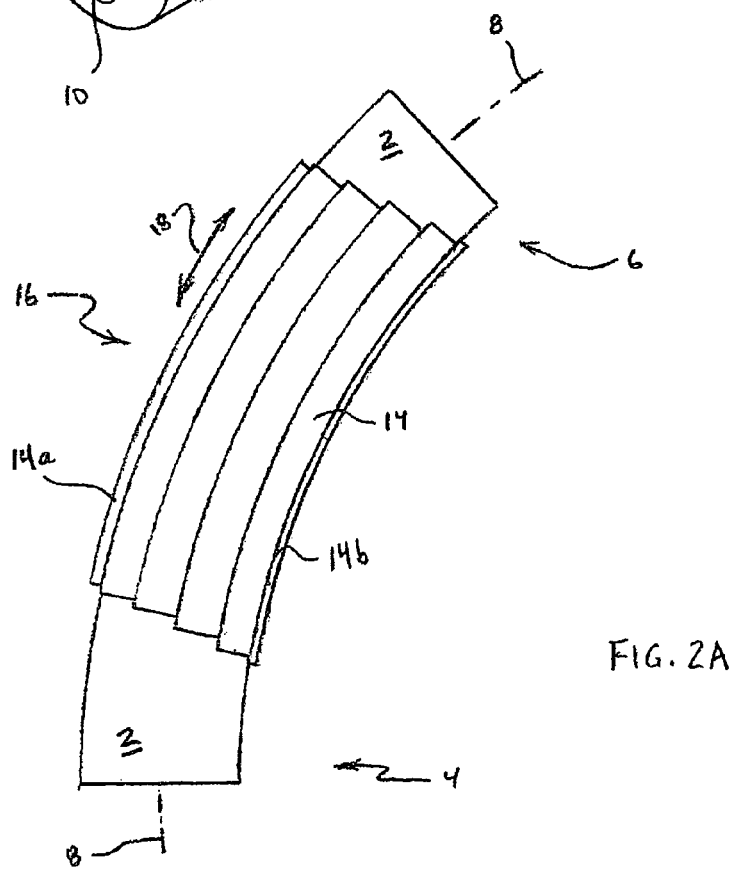
FIGS. 2A and 2B are diagrammatic plan views of longitudinal beams bending and sliding with reference to one another as a guide bends along its longitudinal axis.

In order to provide additional stiffness to guide 2, in accordance with aspects of the invention longitudinal beams 14 are positioned around the outside of the guide as shown in FIG. 1. Various longitudinal beam arrangements and configurations are described in detail below. The arrangement of longitudinal beams is a stiffening assembly 16. Twelve beams 14 are shown arranged around guide 2 in FIG. 1, which is illustrative of various numbers that may be used. Beams 14 are positioned so that an inner face is adjacent the outer surface of guide 2, and so that they are each in sliding contact with one another. Consequently, as guide 2 bends along longitudinal axis 8, the individual beams 14 bend and slide with reference to one another. This feature is illustrated in FIG. 2A, which is a diagrammatic plan view of the surrounding longitudinal beams 14 bending and sliding against one another as guide 2 bends along its longitudinal axis. FIG. 2A shows beams 14 as stationary with reference to each other at roughly half-way between proximal and distal ends, and it can be appreciated that such a stationary relationship can be at the proximal or distal ends, any position between the proximal or distal ends, or at no particular position between the proximal and distal ends. When the beams slide in relation to one another, stiffening assembly 16 is in a flexible state.

In accordance with an aspect of the invention, stiffening mechanism 16 is placed in a stiffened state by compressing the longitudinal beams 14 against each other in a circumferential direction so that friction between the beams effectively prevents the beams from sliding against one another. Accordingly, a mechanical shear force experienced on one side of stiffening assembly 16 is transferred through adjacent, clamped longitudinal beams to the opposite side of the stiffening mechanism. For example, once endoscope 2 is bent as shown in FIG. 2A, with stiffening assembly 16 in a flexible state, then stiffening assembly 16 is placed in a stiffened state by clamping the longitudinal beams against one another. The result is that a shear force, e.g., in an outer bend radius beam 14a, shown as arrow 18, is transferred to an inner bend radius beam 14b by the intervening clamped beams. Consequently, the portion of guide 2 that is covered by stiffening assembly 16 is stiffened, or it is further stiffened if guide 2 has its own stiffening mechanism. Various ways of clamping the beams are described below. When stiffening assembly 16 is unclamped it returns to a flexible state in which the longitudinal beams slide relative to one another, and the portion of guide 2 that is covered by stiffening assembly 16 is once again bendable. Of course, stiffening assembly 16 may provide stiffness when guide 2 is substantially straight as well.

An advantage of stiffening a guide tube/endoscope during surgery is that the increased stiffness is used to counteract the reactive forces on one or more instruments that extend through the guide tube/endoscope. For example, if an instrument that extends through the guide tube/endoscope grasps and pulls tissue, the instrument tends to pull the supporting guide tube/endoscope towards the tissue, thus reducing the effectiveness of the instrument. And, if the instrument suddenly releases the tissue, the guide tube/endoscope tends to snap back to its original position. Stiffening the guide tube/endoscope helps to resist such reactive forces and provides a stable platform for surgical instruments, which makes the instruments more effective during work at the surgical site. This stiffening feature may allow the distal portion of the guide to be cantilevered, thus eliminating the need to brace the distal end of the guide against hard or soft tissue.

Figure 2B:
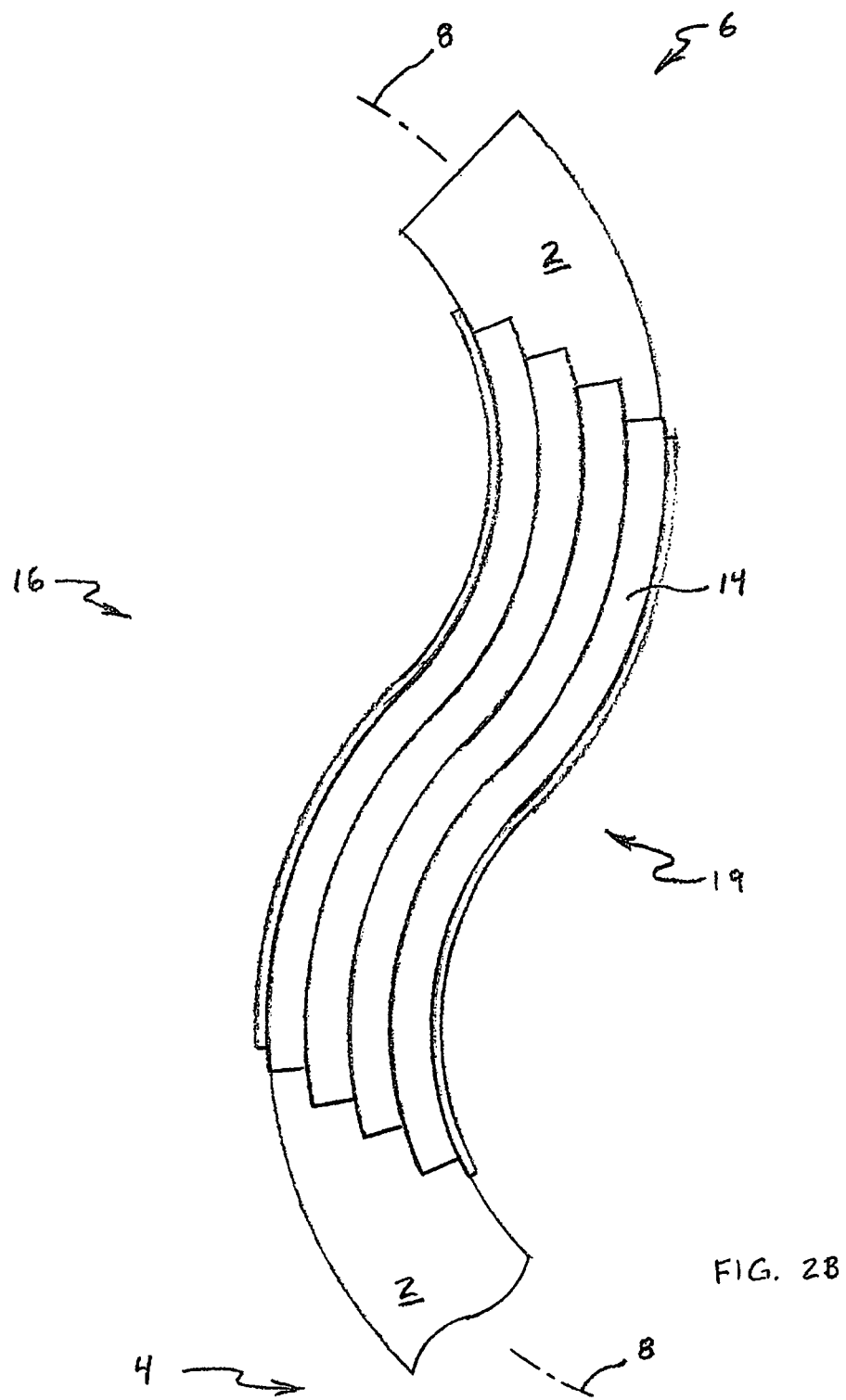

FIG. 2B is another diagrammatic plan view of the longitudinal beams bending and sliding with reference to one another as the guide bends along its longitudinal axis. In the FIG. 2B depiction, the longitudinal beams 14 of the stiffening assembly 16 surround a compound curve in the guide 2. This compound curve illustrates that the stiffening assembly may be configured to accommodate multiple two- or three-dimensional curves in the guide. As shown in FIG. 2B, the longitudinal beams are held stationary with reference to one another at approximately a mid-point between the proximal and distal ends of the beams. In other implementations the beams may be held stationary with reference to one another at other locations along the length of the stiffening assembly. The beams may be held stationary at a particular location by, e.g., anchoring them to the guide. Alternatively, the beams may not be anchored with reference to a particular location along the length of the guide, and instead they can be generally constrained to maintain a sliding relationship along a significant portion of their lengths.

FIG. 3 is an exploded perspective diagrammatic view of bendable longitudinal beams 14 in a stiffening mechanism 6. As shown in FIG. 3, the longitudinal beams 14 are positioned lengthwise around longitudinal axis 8 so as to generally form a tube arrangement. Each longitudinal beam 14 has an inner surface 20 closest to the longitudinal axis 8, an outer surface 22 farthest from the longitudinal axis 8, and two lateral surfaces 24 between inner surface 20 and outer surface 22. As the beams 14 are compressed radially inward towards the longitudinal axis, the surfaces 24 contact each other, and friction between surfaces 24 keeps adjacent beams from moving in relation to one another.

FIGS. 4A-4F are diagrammatic cross-sectional end views that illustrate various cross sectional shapes of the beams themselves and arrangements of the beams around the longitudinal axis 8. As shown in FIG. 4A, in some aspects each longitudinal beam 14 has a substantially rectangular cross section (squares are illustrated).

As shown in FIG. 4B, in some aspects each longitudinal beam 14 is substantially rectangular, and the lateral surfaces 24 are angled so that they contact each other along the full surface of the face. (The illustrated cross-sectional shape is a trapezoid.) This angling increases the lateral surface 24 contact area between adjacent beams, which can result in increased shear transfer capability. FIG. 4B is also illustrative of beams that have an arcuate cross section in the circumferential direction (i.e., either one or both of inner and outer faces 20,22 are curved) so that the lateral surfaces 24 abut one another.

In yet other aspects, each longitudinal beam 14 has a substantially circular cross section as shown in FIG. 4C. A longitudinal beam 14 with a circular cross section can also be considered to have inner, outer, and lateral surfaces 20,22,24, even though such surfaces are not flat. One advantage of such a circular cross section is that larger beams 14 are not subject to instability and non-uniform or asymmetrical deformation that tends to occur when, for instance, an element with a non-round or non-square cross-sectional shape is bent.

FIG. 4D illustrates that the longitudinal beams 14 are not always equidistant from the longitudinal axis 8. For example, beams 14 may be arranged in a roughly elliptical (as shown), oval, or other geometric (e.g., polygonal) cross-sectional shape around the longitudinal axis. FIG. 4D further illustrates that longitudinal beams 14 may be arranged such that the tube structure is more flexible in one plane (e.g., pitch; up and down as shown in the drawing) than in another plane (e.g., yaw; left and right as shown in the drawing). Likewise, if the longitudinal beams 14 are arranged in roughly a square cross-sectional pattern, the stiffness of the tube structure will be generally the same for pitch and yaw, but the tube structure will be stiffer for bends out of the pitch or yaw planes.

FIG. 4E illustrates that the longitudinal beams may be arranged in two or more layers around the longitudinal axis. Accordingly, in a stiffened state shear force is transferred between beams in inner and outer layers, as well as between beams in the same layer. It can be appreciated that FIG. 4E illustrates that each beam 14 may be a small wire or filament, and that such small beams may be loosely packed around a guide, as illustrated in FIG. 4F, so that they frictionally engage each other when compressed together to provide stiffening. For example, one or more layers of 0.010-inch diameter carbon rods may be used.

An internal support structure may be necessary in order to prevent the tube-like structure of the stiffening assembly from collapsing under a bending load (e.g., due to increasing ovalization until a maximum bending moment capacity is reached). In some implementations the guide 2 may provide sufficient support. In other implementations, an intermittent series of inner rings or bulkheads can be used. Or, a helical wound coil may be used to provide continuous internal support. These structures are illustrative of various internal support structures that may be used to prevent the stiffening assembly from collapsing as its radius of curvature decreases.

B. Laminar Construction

Figure 5A:
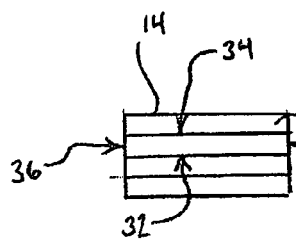
FIGS. 5A-5C are diagrammatic cross-sectional end views of various laminar longitudinal beams.
Figure 5B:
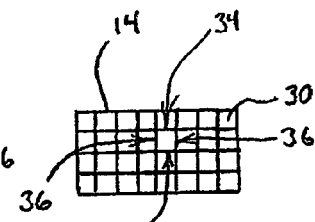
Figure 5C:
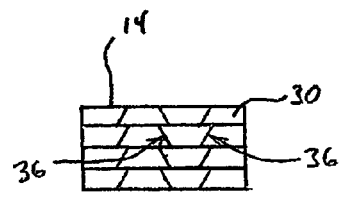

In a further aspect of the invention, each longitudinal beam 14 may be made of two or more longitudinal laminar elements (laminae). FIGS. 5A-5C are diagrammatic cross-sectional end views of various laminar longitudinal beams 14.

As shown in FIG. 5A, longitudinal beam 14 is made of several planar laminae 30 stacked on one another in a radial direction. Each lamina 30 has an inner (towards the tube's centerline; longitudinal axis) surface 32, an outer (away from the tube's centerline; longitudinal axis) surface 34, and two lateral surfaces 36. Example dimensions are 0.040-inch wide and 0.010 inch thick. The laminae 30 are not permanently fixed to one another, so that as longitudinal beam 14 bends in a flexible state, the laminae 30 slide in relation to one another. Accordingly, when the laminae 30 are allowed to slide, the laminar longitudinal beam 14 as illustrated in FIG. 5A has a pitch stiffness that is less than a similarly sized monolithic longitudinal beam made of substantially the same material.

FIG. 5B shows that the laminae 30 may be arranged in a circumferential direction, or that laminae stacked in a radial direction may be subdivided in a circumferential direction. As shown, the laminae 30 each have a generally square cross section and are arranged in a 4×8 (the numbers and shapes are merely illustrative) matrix so that longitudinal beam 14 has a generally rectangular cross section. Again, each lamina 30 may slide in relation to the others so that longitudinal beam 14's stiffness is reduced in more than one plane. Such an arrangement helps reduce or eliminate the tendency of a rectangular cross-sectional beam to twist as it is bent in the plane of its long side, because the lateral surfaces 36 of the laminae 30 may slide against each other. Reference is made again to FIGS. 4E and 4F, which also illustrate the notion of many small laminar beams forming a larger beam, and that the individual laminae may have circular or other rounded cross-sectional shapes.

FIG. 5C illustrates that the laminae 30 may have cross sections that interlock to further control twisting as longitudinal beam 14 bends in various directions. As shown in FIG. 5C, the cross sections of the laminae 30 are generally trapezoidal so that the lateral surfaces 36 of each lamina are angled against each other. Consequently, the laminae 30 generally engage two or more adjacent laminae 30 as longitudinal beam 14 bends in various directions. Example dimensions: the laminae are approximately 0.025-inch wide, approximately 0.005-inch thick, and the lateral surfaces are angled at approximately 45 degrees.

Figure 6A:
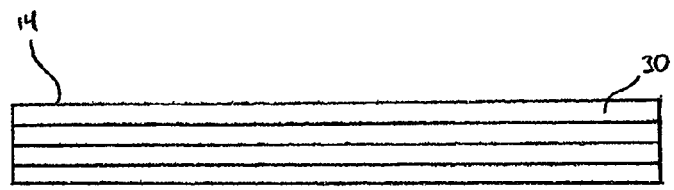
FIGS. 6A-6D are diagrammatic side views of various illustrative laminar longitudinal beam configurations.
Figure 6B:
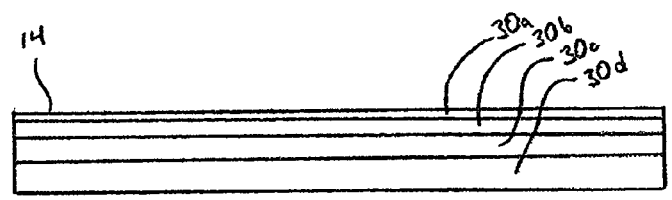

FIGS. 6A-6D are diagrammatic side views of various illustrative laminar longitudinal beam 14 configurations. As shown in FIG. 6A, the laminae 30 are substantially the same thickness, and each one extends for the length of longitudinal beam 14. In FIG. 6B, the laminae 30 are substantially the same length, but each lamina has a different thickness. As shown, laminae 30a-30d become progressively thicker towards the longitudinal axis 8 (not shown). Example dimensions: lamina 30a is 0.001-inch thick, 30b is 0.002-inches thick, 30c is 0.003-inches thick, and 30d is 0.004-inches thick. Top, bottom, or middle laminae may be thicker than the others, depending on desired longitudinal beam stiffness qualities.

Figure 6C:
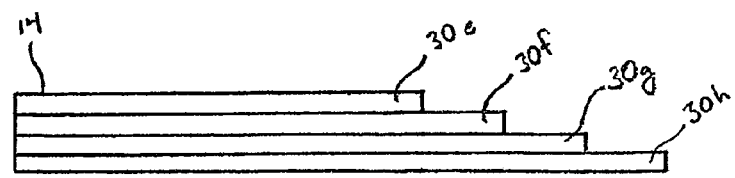
Figure 6D:
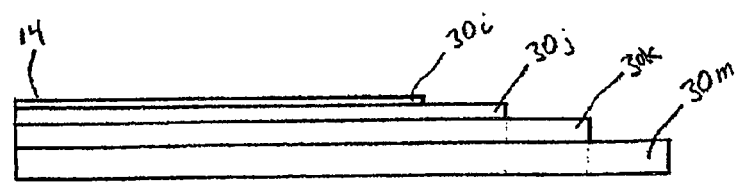

FIGS. 6C and 6D illustrate that the longitudinal beams may be configured to have varying stiffness along their length. In one case, monolithic longitudinal beams may be tapered from one end to another so that the beam stiffness at the relatively thinner end is less than the beam stiffness at the relatively thicker end. Alternatively, as illustrated by FIGS. 6C and 6D, the length of the laminae 30 may be varied to vary the stiffness along the length of a beam 14. FIG. 6C shows progressively longer laminae 30e-30h so that longitudinal beam 14 becomes progressively less stiff as it becomes made of fewer laminae. FIG. 6D illustrates a similar configuration, except that the thickness of the progressively longer laminae 30i-30m varies so that the stiffness of beam 14 can be configured as desired. Skilled artisans will understand that longitudinal beam 14 stiffness may increase from distal to proximal ends, and vice-versa. And, the lengths of individual laminae may be varied in the circumferential direction so that laminae at one lateral side of the beam or at a middle location are longer that laminae at the opposite lateral side of the beam.

The cross section of the individual beams or laminae must be small enough to permit a desired minimum bend radius without exceeding the yield strength of the beam material. The use of two or more layers of longitudinal beams, as illustrated by FIGS. 4E and 4F, may serve to allow the stiffening assembly to be bent in a smaller bend radius and/or bent with less force while in the flexible state, without reducing its stiffness in the stiffened state.

C. Clamping

As described above, the longitudinal beams of the stiffening assembly are bendable and slide in relation to one another. Once the stiffening assembly is bent into a desired configuration, the beams and/or laminae are clamped against one another and/or against a support structure (e.g., a bulkhead) in order to stiffen the assembly.

Accordingly, it is desirable that the longitudinal beams and laminae be a high strength, high modulus of elasticity material, such as high-strength steel or super alloy, or a carbon/epoxy composite. It may also be desirable to use materials or surface coatings for the beams and laminae that achieve a relatively large static coefficient of friction when clamped and a relatively low dynamic coefficient of friction when unclamped. If materials or coatings are chosen such that the coefficient of static friction is significantly higher than the dynamic coefficient of friction at low speeds, then the stiffening assembly will have an extremely high stiffness in a stiffened state when clamped along the length of a longitudinal beam (e.g., using a vacuum, as described below) and a relatively low resistance to bending in a non-stiffened state when clamping is released.

As described above, clamping the surfaces of individual beams against one another transfers shear forces from one side of the stiffening assembly to the other to stiffen the assembly, and clamping laminae together transfers shear forces within a beam to stiffen the beam. Since the stiffness of a beam in bending is proportional the cube of its thickness parallel to the direction of the applied bending force, a clamped laminar beam may have a bending stiffness 100 times larger—or more—than when unclamped. The stiffness increase depends on the beam dimensions, and to some extent the laminar configuration of the beams when applicable, as well as on the clamping force and area clamped.

In accordance with an aspect of the invention, a vacuum is used to clamp monolithic or laminar beams together in order to accomplish shear transfer along the length of the beam, or along a significant portion of the length. The vacuum can also be used to clamp laminae in individual beams together to stiffen the beams.

FIG. 7A is a diagrammatic cross-sectional view that shows longitudinal beams 14 arranged in a stiffening assembly 16 around longitudinal axis 8. The longitudinal beams 14 are positioned between an inner wall 40 and an outer wall 42. In one aspect the longitudinal beams 14 free float between the inner and outer walls 40,42. The inner and outer walls 40,42 are flexible so that the stiffening assembly may bend. A vacuum introduced in the space 44 between the walls causes the longitudinal beams 14 to be clamped between the walls, thereby stiffening the assembly in its current curved configuration. If applicable, the introduced vacuum also causes the walls to clamp the laminae in the beams. In one aspect, inner wall 40 is the outer surface of the guide 2 (FIGS. 1 and 2A-2B), such as the outer surface of a flexible, steerable endoscope. It can be appreciated that depending on various configurations, a vacuum between the walls may cause a compression force radially inwards towards the longitudinal axis, radially outwards away from the longitudinal axis, or both.

In some aspects the space 44 between the inner and outer walls is filled with a gas in the unclamped (non-stiffened) state, which is evacuated in the clamped (stiffened) state. In other aspects, space 44 may be filled with a liquid 45. Referring to the top detail view in FIG. 7A, during the unclamped state, a thin film 46 of the liquid acts as a lubricant between beams 14 and/or laminae 30. This thin film facilitates bending by providing hydrodynamic lubrication between surfaces of the beams and laminae, which greatly reduces dynamic friction between the sliding surfaces. Referring to the bottom detail view in FIG. 7A, during the clamped state the liquid is effectively evacuated, and the surfaces of the beams and laminae contact one another. The contact results in boundary lubrication between contacting surfaces with a corresponding higher coefficient of friction, thus greatly stiffening the assembly. The introduction and evacuation of a lubricating fluid between the sliding surfaces allows both the "stick" and "slip" characteristics of the mechanical stick-slip phenomenon to be used to advantage in the stiffening mechanism.

For use in a surgical device, the liquid may be a biocompatible lubricant, e.g., water, alcohol or a fluid as described in U.S. Pat. No. 7,060,199 B2 (filed 22 Dec. 2004), which is incorporated herein by reference. Water is effective because of its relatively low surface tension and ease of effectively complete evacuation; alcohol, even more so. One or both opposing surfaces of the walls may have protrusions or other structures (e.g., ribs, channels, and the like) that facilitate complete evacuation of the gas or liquid from space 44. In some aspects, the protrusions or other structures may assist holding the beams and/or laminae in place between the inner and outer walls.

FIGS. 7B and 7C are diagrammatic cross sectional detail views of another implementation of hydrodynamic lubrication. As shown in FIG. 7B, a lubricating fluid 47 is introduced between longitudinal filaments 48, which are illustrative of beams or laminae. This lubricating fluid helps to displace the walls 42 and 44 apart, providing room for the filaments to separate, and it provides a hydrodynamic lubrication between the filaments when the stiffening assembly is in an unclamped, flexible state. As shown in FIG. 7C, the fluid is effectively removed so that the filaments contact one another, and when a clamping force is applied radially to the longitudinal filaments, the stiffening assembly is placed in a clamped, stiffened state.

FIG. 8 is a schematic view of a vacuum clamping system for a minimally invasive surgical assembly 50. As shown in FIG. 8, a minimally invasive surgical instrument 52 extends through guide 2. Guide 2 helps guide instrument 52 towards a surgical site within a patient. In one illustrative aspect, guide 2 has an outside diameter on the order of 15-18 mm. Either guide 2 or instrument 52, or both, may be an endoscope. Surgical instruments extending through an endoscope or guide tube are further illustrated by U.S. Patent Application Pub. No. US 2008/0065105 A1 (filed 13 Jun. 2007), which is incorporated by reference. The assembly represented by FIG. 8 is illustrative of a general configuration using other clamping implementations as well.

As depicted in FIG. 8, a vacuum-operated stiffening assembly 16 is positioned around a distal portion of guide 2. As described above, vacuum source 54 evacuates space 44 to clamp longitudinal beams 14. Optional pressure source 53 provides gas or liquid insufflation, as described above when the stiffening assembly is in its unclamped, flexible state. Introducing the lubricating liquid under pressure helps form the lubricating film between sliding surfaces. Vacuum source 54 provides, e.g., 10 psi of vacuum, which is available from typical commercially available vacuum sources. Vacuum source 54 is used to effectively evacuate the gas or liquid and bring the sliding surfaces into contact with one another.

During a surgical procedure, the guide 2 is introduced into the patient and is steered towards a surgical site 55 (e.g., in the abdomen or thorax). Once the distal end of the guide is positioned in a working position and orientation at the surgical site, the stiffening assembly 16 is used to stiffen the guide to maintain the desired position and orientation. When the distal portion of guide is stiffened by stiffening assembly, the distal portion provides a stable, cantilever platform for instrument 52 to work at the surgical site. This platform is stable against tissue reactive forces against end effector 56 during a surgical procedure. End effector 56 is illustrative of, e.g., graspers, needle drivers, scissors, retractors, electrocautery electrodes, and the like.

An advantage of using a vacuum to clamp the longitudinal beams is that the vacuum may be quickly released by venting the evacuated space to the surrounding ambient atmosphere. Or, the space between the clamping walls may be insufflated with a small positive pressure to help the beams and the laminae freely slide when the flexible tube is repositioned.

FIG. 8 also illustrates that one or more microvalves may be used to aid insufflation and evacuation of fluid in the vacuum clamping stiffening assembly. As shown in FIG. 8, an illustrative microvalve 57 is positioned at or near the distal end of the stiffening assembly. The microvalve assembly may contain a sensor that senses the presence of a fluid. During insufflation, the microvalve at the distal end is opened to allow any ambient gas (e.g., air) in the stiffening assembly to escape as, e.g., a liquid is introduced into the proximal end of the stiffening assembly by pressure source 53. If a sensor is used, then the sensor can generate a signal to close the microvalve when the sensor detects the insufflation fluid. Alternatively, the microvalve may be closed in accordance with another parameter, such as elapsed insufflation time. During evacuation, the microvalve may be opened to allow ambient air to enter the stiffening assembly, thus assisting evacuation of the liquid. The operation of the pressure source, the vacuum source, and the microvalve may be coordinated by an electronic controller 58 (e.g., microprocessor-based). The controller may operate each component separately.

Although vacuum clamping has some noteworthy characteristics, other clamping methods may be used. In some aspects, discussed below, the longitudinal beams may not contact each other when the stiffening assembly is in a stiffened state. In this situation, shear force from one beam is transferred to another beam via an intermediate structure. For example, shear forces may be transferred from one side of a stiffening assembly via bulkheads rather than directly between adjacent longitudinal beams.

FIG. 9 is a diagrammatic perspective view of another aspect of a stiffenable assembly 16 in accordance with the invention. Two illustrative annular support bulkheads 60 are shown. Each bulkhead 60 has a number of holes 62 arranged to allow longitudinal beams 14 to pass through. Only a single longitudinal beam 14 is shown so that the bulkheads may be seen with more clarity, and it should be understood that longitudinal beams 14 extend though all holes 62. In some instances holes 62 are generally shaped to allow a close and sliding fit for longitudinal beams 14. And, if longitudinal beams 14 are made of individual laminae, as described above, then the individual laminae may slide with reference to one another as the assembly bends. In other instances, longitudinal beams 14 may be anchored (e.g., glued, welded, friction fit, etc.) within holes 62 of one bulkhead so that neither they nor their laminae slide. Bulkheads 60 are also shown having a large central hole 64, which is illustrative of various numbers of other such holes that may allow passage of, e.g., guide 2, or other surgical device, or control cables for distal surgical instrument end effectors.

FIG. 9 also shows a clamping mechanism 66 that is used to clamp the beams 14 against the bulkheads 60 and to clamp the laminae 30 against one another. As shown in FIG. 9, one implementation of clamping mechanism 66 is a split ring that may be radially expanded to compress each longitudinal beam 14 against the outer surfaces of the holes 62 in bulkhead 60. This split ring is illustrative of various mechanisms and mechanical configurations that may be used to clamp the beams.

FIG. 10A is a diagrammatic cross-sectional view that illustrates one aspect of clamping mechanism 66. As shown in FIG. 10A, an activating cable 68 (or rod, or other suitable mechanical linkage) passes through bulkhead 60 and is connected to wedge 70 by the use of a swaged/crimped fitting 72 or other suitable way. When tension is applied to cable 68, the inclined surface of wedge 70 engages clamping mechanism 66 and forces it outward, thus compressing beam 14 and laminae 30 against bulkhead 60. Wedge 70 is illustrative of both a single chamfered ring that generally concentrically engages clamping mechanism 66, and of numerous single wedges that engage clamping mechanism 66 near each hole 62 in bulkhead 60. FIG. 10A shows clamping mechanism 66 compressing beam 14 and laminae 30 outwards, away from the center of the stiffening assembly 16, but it can be seen that the configuration can be easily modified to compress the beams and laminae radially inwards.

FIGS. 10B-10D are diagrammatic cross-sectional views that illustrate other aspects and implementations of clamping mechanisms. As shown in FIG. 10B, cable 74 passes through wedge structure 76 and is connected to clamping mechanism 78. As tension is applied to cable 74, clamping mechanism 78 is drawn towards wedge structure 76, which forces clamping mechanism 78 against longitudinal beam 14 and compresses beam 14 and laminae 30 against bulkhead 60. In some aspects wedge structure 76 is part of bulkhead 60. In other aspects, wedge structure 76 may be attached to (or be an integral part of) the lamina 30 against which clamping mechanism 78 presses.

FIG. 10C illustrates another aspect of activating a clamping mechanism. As shown, cable 80 is routed from the inside to the outside (or vice versa) of bulkhead 60 to engage clamping mechanism 78. Cable 80 enters bulkhead 60 though a passage, passes over, e.g., a pulley or a fairlead (either of the two may be used, with consideration being given to friction) to extend outward, and then passes over another pulley or fairlead in wedge structure 76 to engage clamping mechanism 78. Pulley 82 and fairlead 84 as shown in FIG. 7B are illustrative of the positioning of such cable routing components.

FIG. 10D illustrates yet another aspect of activating a clamping mechanism. As shown in FIG. 10D, cable 86 inserts into bulkhead 60, passes over pulley 88 (or a fairlead or other guiding structure), and extends radially outward to engage clamping mechanism 90. When tension is applied to cable 86, clamping mechanism 90 is pulled inward against longitudinal beam 14, which compresses beam 14 and laminae 30 against bulkhead 60.

It can be seen from the various aspects illustrated by FIGS. 10A-10D, that there are many possible ways of applying a force either radially inwards or outwards to clamp the beams to a bulkhead and to compress the laminae against each other, thereby enabling shear transfer to increase the stiffness of the stiffening apparatus. Other clamping mechanisms may include, e.g., the use of a shape memory alloy (SMA) that when heated (e.g., by use of an electrical current) expands to change a clamping state of the longitudinal beams (i.e., either the clamped or unclamped state exists when the SMA is heated, depending on the design configuration).

Figure 11:
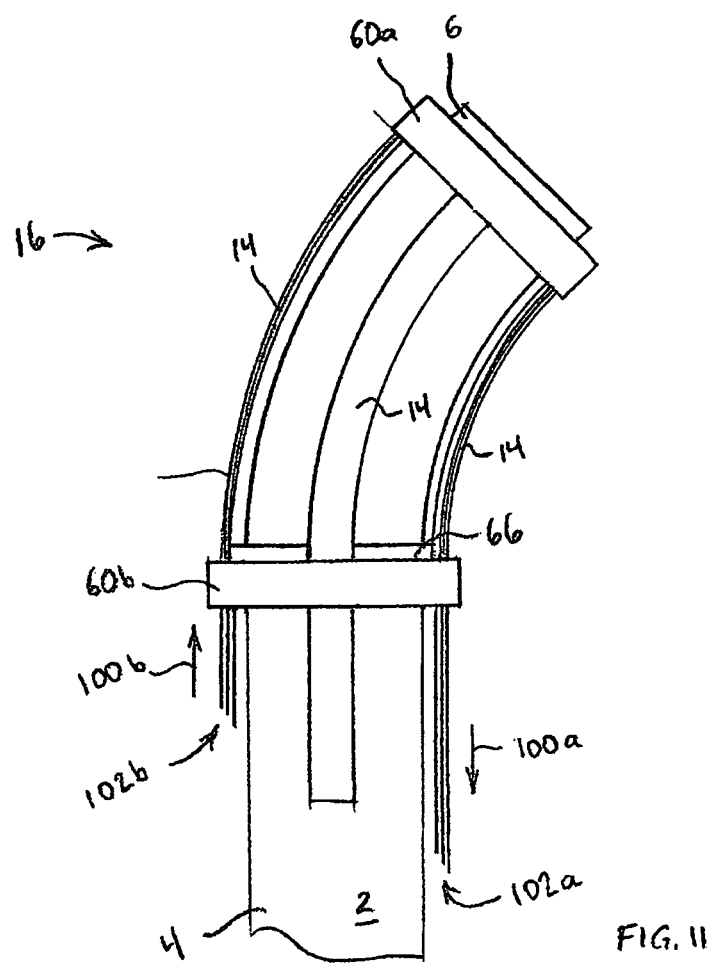
FIG. 11 is a diagrammatic view that illustrates another implementation of a stiffening assembly positioned around a distal portion of a steerable, bendable guide.

FIG. 11 is a diagrammatic view that illustrates another implementation of a stiffening assembly 16 in accordance with aspects of the invention. FIG. 11 depicts a stiffening assembly, as generally described with reference to FIG. 9, positioned around a distal portion of a steerable, bendable guide 2. FIG. 11 depicts a configuration in which four longitudinal beams 14 are equidistantly spaced around guide 2 (one beam is hidden from view behind the guide). This configuration is illustrative of various configurations in which two, three, or more (e.g., 12) longitudinal beams are used. A large number of longitudinal beams is not shown in the figure so that the principles of various aspects of the invention can be clearly seen.

Bulkhead 60a is coupled to guide 2 near its distal end 6. The distal ends of longitudinal beams 14 are anchored in bulkhead 60a. A second bulkhead 60b is coupled to guide 2 at a location proximal of bulkhead 60a. The two bulkheads 60 shown in FIG. 11 are illustrative of various numbers of bulkheads that may be used to guide and support, and optionally clamp, the longitudinal beams.

As the distal part of guide 2 bends, e.g., to the right as depicted in FIG. 11, longitudinal beams 14 slide through holes in bulkhead 60b as described above. Thus the longitudinal beam at the inside of the guide's bend slides proximally through bulkhead 60b, as shown by arrow 100a. Similarly, the longitudinal beam at the outside of the guide's bend slides distally through bulkhead 60b, as shown by arrow 60b. In addition, the individual laminae of the longitudinal beams at the inside and outside of the guide's bend slide against one another. The laminae farthest from the guide's central longitudinal axis slide the farthest, as shown by arrows 102a (inner curve) and 102b (outer curve). When guide 2 is at a desired bend angle, then clamping mechanism 66 is actuated as described above (components such as cables are omitted from the drawing for clarity) to clamp the beams against the bulkhead and the laminae against one another. Accordingly, when the stiffening mechanism is clamped, lateral forces acting on the guide's distal end cause shear forces within one or more longitudinal beams, and these shear forces are transferred from the beam, through the bulkhead(s), to one or more beams on the opposite side of the guide.

FIG. 11 shows only the distal end of guide 2, but it can be appreciated that with longer longitudinal beams and more bulkheads, various lengths of the guide can be stiffened by using a stiffening assembly in accordance with aspects described herein. Further, by actuating different clamping implementations at various bulkheads, one or more portions of the guide may be stiffened while one or more other portions remain flexible. For example, in a three-bulkhead arrangement, if the longitudinal beams are held stationary with reference to the middle bulkhead, then the proximal section of the guide bounded by the most proximal and middle bulkheads may be stiffened by clamping at the proximal bulkhead. Similarly, the distal section bounded by the middle and most distal bulkheads can be stiffened by clamping at the distal bulkhead. And, with reference to FIGS. 6C and 6D above, it can be appreciated that by varying the laminar composition of the longitudinal beams, various stiffnesses can be applied to various parts of the guide. It can be seen that using separate stiffening assemblies for two or more portions of the guide may be implemented with vacuum clamping, as well as various other ways to clamp the beams and laminae.

A flexible sheath may be placed over the stiffening assembly to prevent tissue damage as the guide moves within a patient or to prevent body fluids and tissue from entering the stiffening assembly.

The longitudinal beam clamping described with reference to FIGS. 9-11 occurs over a relatively small proportion of the beam. The stiffness of the stiffening assembly is dependent on the amount of shear transfer that can occur between beams, and the stiffness of a laminar beam is dependent on the amount of friction and clamping force that can be generated between the laminae. It can be seen that a vacuum clamping mechanism, such as illustrated in FIG. 8, may provide relatively higher inter-beam and inter-lamina shear transfer, and thus more assembly and beam stiffness, than the clamping mechanism illustrated in FIGS. 10A-10D, because it creates clamping force over a larger area between beams and laminae. Accordingly, in general, the larger the clamping area on the longitudinal beam, the stiffer the beam.

It can be seen that a stiffenable assembly in accordance with aspects of the invention may have significant benefits to minimally invasive surgery, and particularly to telerobotic surgery done in the manner of the da Vinci® Surgical System, manufactured by Intuitive Surgical, Sunnyvale, Calif.

Aspects may be used to stiffen and hold a guide tube in a fixed shape to provide a platform against tissue reactive forces from surgical instruments that are supported by the guide.

I claim:

1. A stiffening assembly comprising:
   a plurality of longitudinal beams positioned in a bendable tube-like arrangement around a longitudinal axis; and
   a clamping mechanism;
   wherein in a first clamping mechanism state the beams are clamped in a substantially fixed position relative to one another; and
   wherein in a second clamping mechanism state the beams longitudinally slide relative to one another.

2. The stiffening assembly of claim 1: wherein in the first clamping mechanism state the beams are clamped against one another.

3. The stiffening assembly of claim 1: wherein in the first clamping mechanism state the beams are clamped against a bulkhead.

4. The stiffening assembly of claim 1: wherein a longitudinal beam is a laminar beam comprised of a plurality of longitudinal laminar elements.

5. The stiffening assembly of claim 4: wherein in the first clamping state the clamping mechanism clamps the laminar elements against one another.

6. The stiffening assembly of claim 4: wherein lengths of the laminar elements in the laminar beam are different from one another.

7. The stiffening assembly of claim 4: wherein thicknesses of the laminar elements in the laminar beam are different from one another.

8. The stiffening assembly of claim 4: wherein the plurality of laminar elements comprises a plurality of filaments.

9. The stiffening assembly of claim 1: wherein the plurality of longitudinal beams comprises a plurality of filaments.

10. The stiffening assembly of claim 1: wherein the clamping mechanism comprises a vacuum source.

11. The stiffening assembly of claim 1: wherein the clamping mechanism applies force radially outward from the longitudinal axis.

12. The stiffening assembly of claim 1: wherein the clamping mechanism applies force radially inward from the longitudinal axis.

13. The stiffening assembly of claim 1 further comprising:
    a support structure positioned to prevent collapse of the tube-like arrangement when the stiffening assembly is subjected to a bending load.

14. A surgical instrument assembly comprising:
    a stiffening assembly positioned around a flexible guide, wherein the stiffening assembly comprises a plurality of longitudinal beams positioned around a longitudinal axis, and a clamping mechanism; and
    a surgical instrument extending through the guide;
    wherein a first clamping mechanism state holds the guide in a desired curved shape by clamping the beams in a substantially fixed position relative to one another; and
    wherein a second clamping mechanism state allows the guide to change curvature by allowing the beams to longitudinally slide relative to one another.

15. The surgical instrument assembly of claim 14: wherein each of the longitudinal beams is comprised of laminar elements;
    wherein the first clamping mechanism state clamps the laminar elements of each beam in a substantially fixed position relative to one another; and
    wherein the second clamping mechanism state allows the laminar elements of each beam to slide relative to one another.

16. A method of stiffening a flexible device, comprising:
    inducing a first state in which a plurality of longitudinal beams positioned in a bendable tube-like arrangement around a longitudinal axis are clamped in a fixed position relative to one another; and
    inducing a second state in which the beams longitudinally slide relative to one another.

17. The method of claim 16: wherein inducing the first state comprises clamping the beams against one another.

18. The method of claim 16: wherein inducing the first state comprises clamping the beams against a bulkhead.

19. The method of claim 16: wherein inducing the first state comprises inducing a vacuum.

20. The method of claim 16: wherein inducing the first state comprises
    inducing a state in which laminar elements of a beam are clamped against one another; and,
    wherein inducing the second state comprises inducing a state in which the laminar elements slide relative to one another.

21. The method of claim 16: wherein the device comprises a flexible guide for a surgical instrument.

22. The method of claim 16 further comprising:
    steering a distal end of the guide to a position near a surgical site during the second state;
    inducing the first state when the distal end of the guide is near the surgical site; and,
    operating a surgical instrument extended through the guide during the first state.

23. A method of stiffening a flexible guide, comprising:
    introducing a lubricating fluid between adjacent surfaces of longitudinal beams positioned in a bendable tube-like arrangement around a longitudinal axis; and
    effectively evacuating the fluid from between the adjacent surfaces of the beams.

24. The method of claim 23 further comprising:
    introducing the fluid between adjacent surfaces of laminae in one of the longitudinal beams; and
    effectively evacuating the fluid from between the adjacent surfaces of the laminae.

25. The method of claim 23: wherein a first frictional force resisting relative motion between two adjacent beams consists essentially of dynamic friction when the fluid is introduced; and,
    wherein a second frictional force resisting relative motion between two adjacent beams consists essentially of static friction when the fluid is effectively evacuated.

26. The method of claim 23 further comprising:
    steering a distal end of the guide to a position near a surgical site while the fluid is between the adjacent surfaces of the beams;
    effectively evacuating the fluid when the distal end of the guide is near the surgical site; and,
    operating a surgical instrument extended through the guide while the fluid is effectively evacuated.

* * * * *